(12) United States Patent
Buesseler

(10) Patent No.: US 12,042,609 B2
(45) Date of Patent: Jul. 23, 2024

(54) MEDICAL DEVICE INCLUDING AN ACTUATOR RESTRAINING ASSEMBLY

(71) Applicant: St. Jude Medical, Cardiology Division, Inc., St. Paul, MN (US)

(72) Inventor: Ryan Kenneth Buesseler, Delano, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 780 days.

(21) Appl. No.: 17/222,071

(22) Filed: Apr. 5, 2021

(65) Prior Publication Data

US 2021/0220611 A1 Jul. 22, 2021

Related U.S. Application Data

(62) Division of application No. 16/136,411, filed on Sep. 20, 2018, now Pat. No. 10,994,098.

(60) Provisional application No. 62/560,778, filed on Sep. 20, 2017.

(51) Int. Cl.
*A61M 25/01* (2006.01)

(52) U.S. Cl.
CPC .... *A61M 25/0147* (2013.01); *A61M 25/0113* (2013.01); *A61M 25/0136* (2013.01); *A61M 2025/015* (2013.01)

(58) Field of Classification Search
CPC .......... A61M 25/0147; A61M 25/0113; A61M 25/0136; A61M 2025/015
See application file for complete search history.

(56) References Cited

U.S. PATENT DOCUMENTS

| | | | |
|---|---|---|---|
| 8,118,803 B1 | 2/2012 | Chow | |
| 8,137,308 B2 | 3/2012 | Schultz | |
| 9,278,191 B2 | 3/2016 | Nihonmatsu et al. | |
| 2010/0280316 A1 | 11/2010 | Dietz et al. | |
| 2010/0286480 A1 | 11/2010 | Peine et al. | |
| 2014/0171803 A1 | 6/2014 | Van Hoven et al. | |

*Primary Examiner* — Amber R Stiles
(74) *Attorney, Agent, or Firm* — Armstrong Teasdale LLP

(57) ABSTRACT

The present disclosure provides a means of holding, securing, or self-locking an actuating mechanism, such as a plunger-type or slide-type actuating mechanism, on a medical device having a deflected distal region using pinch points without the need for a secondary restraining or locking mechanism within the medical device. The present disclosure also provides a means to reduce the force experienced by a user during the deflection of a medical device such that use fatigue is lessened or eliminated. Various embodiments of the present disclosure are set forth herein.

20 Claims, 6 Drawing Sheets

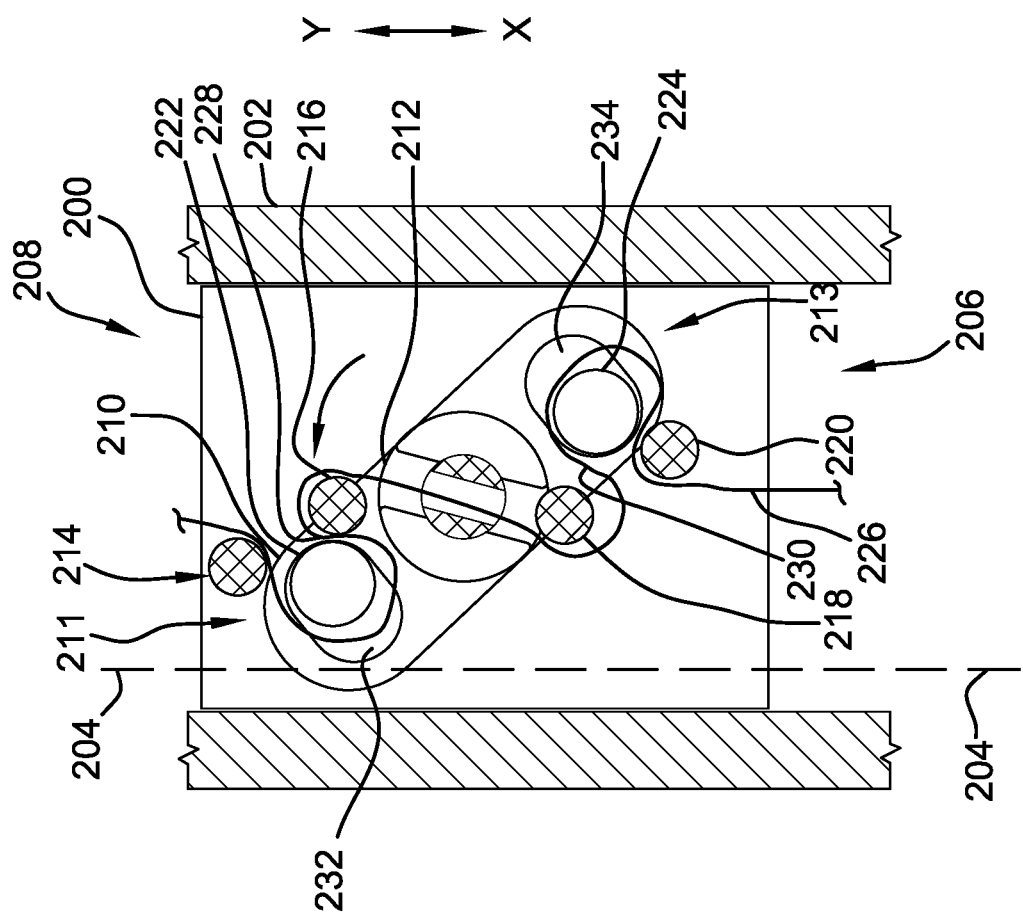
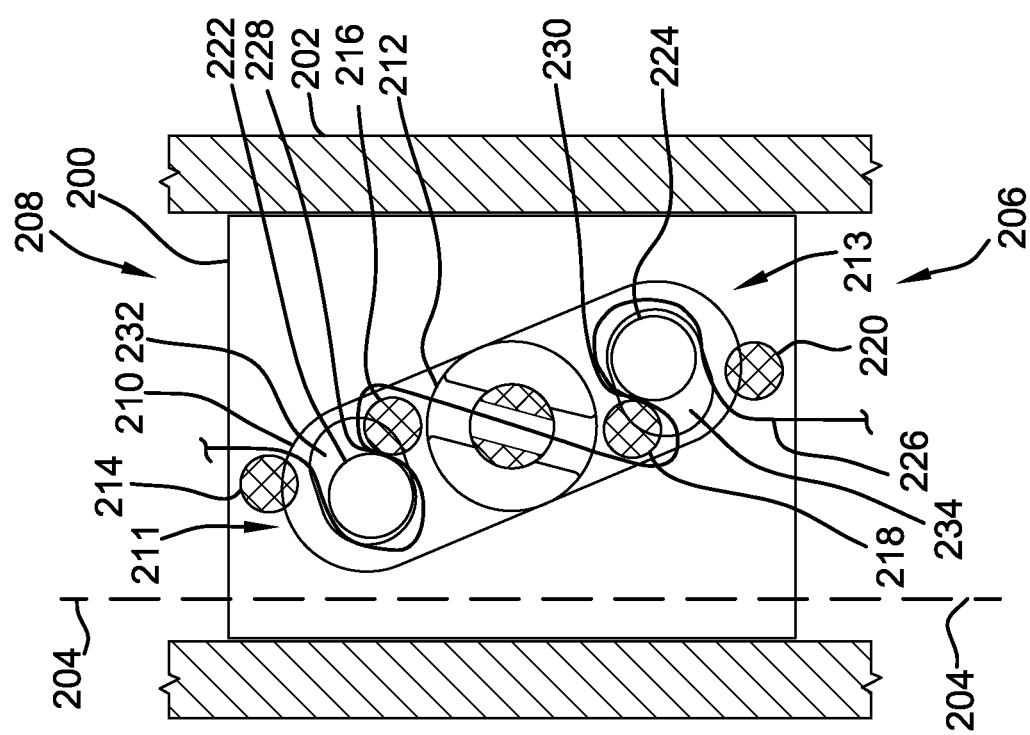

MEDICAL DEVICE INCLUDING AN ACTUATOR RESTRAINING ASSEMBLY

A. CROSS REFERENCE OF RELATED APPLICATION

This application is a divisional of U.S. application Ser. No. 16/136,411, filed Sep. 20, 2018, which claims priority to U.S. Provisional Application Ser. No. 62/560,778, filed Sep. 20, 2017 both of which are incorporated by reference herein in their entirety.

B. FIELD OF THE DISCLOSURE

The present disclosure relates generally to medical devices that are used in the human body. In particular, in many embodiments, the present disclosure relates to a medical device actuator restraining assembly for assisting in holding, retaining, and/or locking a medical device actuator mechanism in a desired position during use while allowing the release of the medical device actuator mechanism to another position as desired. The present disclosure may be particularly useful in plunger-type and slide-type uni-directional and bi-directional catheter handles for deflection of a distal region.

C. BACKGROUND

Medical devices, such as catheter systems, are well known in the art for use in medical procedures, such as diagnostic (e.g., cardiac mapping) and therapeutic procedures (e.g., cardiac ablation). Typical catheter systems generally include an elongated flexible catheter shaft extending from a control handle containing an actuating mechanism. A physician manipulates the catheter shaft through the patient's vasculature to an intended site within the patient via the actuating mechanism contained within the control handle.

An actuating mechanism of the catheter system may include mechanical steering features or components that may be manually manipulated to position a catheter shaft within the body at a desired site or to operate the catheter system during use. In some embodiments, a catheter or catheter system may be positioned within a patient's vasculature during a procedure by simultaneous application of torque or force at the proximal end of the catheter and/or by selectively deflecting the distal tip of the catheter in a desired direction.

The distal tip of the catheter can be deflected by a pull wire or other tension member attached or anchored at the distal end of the catheter and extending proximally to an actuator mechanism in a control handle that controls the application of tension on the pull wire. Distal movement of the catheter shaft with respect to a body of the control handle, upon the application of an external force on the actuating mechanism, may impose eccentric pull forces on the distal portion of the catheter shaft resulting in the distal portion of the catheter shaft assuming a deflected configuration. Absent an external force exerted on the actuating mechanism, the catheter shaft tends to return to its natural, unstressed neutral position due to the force exerted on it by the strained pull wire.

BRIEF SUMMARY OF THE DISCLOSURE

The present disclosure provides a means of holding, securing, or self-locking an actuating mechanism, such as a plunger-type or slide-type actuating mechanism, on a medical device having a deflected distal region without the need for a secondary restraining or locking mechanism within the medical device by using various pull wire pinch points. The present disclosure also provides a means to reduce the force experienced by a user during the deflection of a medical device such that use fatigue is lessened or eliminated. Various embodiments of the present disclosure are set forth herein.

In one embodiment, the present disclosure is directed to a medical device having a deflectable distal region. The medical device comprises: (i) a handle; (ii) an actuator restraining assembly including a moveable assembly disposed in the handle and configured to slide along a longitudinal axis within the handle, the moveable assembly comprising: (a) a first pinch member; (b) a second pinch member; (c) a first tension member configured to be in contact with the first pinch member; (d) a second tension member configured to be in contact with the second pinch member; and (e) a central block portion configured to be positioned between the first pinch member and the second pinch member and in contact with the first pinch member and the second pinch member such that longitudinal movement of the moveable assembly and central block portion in a first direction causes the first tension member to move to a compressed position and movement of the central block portion in a second direction causes the second tension member to move to a compressed position.

In another embodiment, the present disclosure is directed to a medical device. The medical device comprises: (i) a handle; (ii) a catheter shaft having a proximal region and a deflectable distal region; (iii) an active drive assembly comprising a split actuator mechanism including a distal actuator mechanism and a proximal actuator mechanism, wherein the split actuator mechanism is configured to engage the proximal region of the catheter shaft and is at least partially movable with respect to a handle along a longitudinal axis thereof; and (iv) an actuator restraining assembly comprising: (a) a moveable assembly disposed in the handle and fixedly coupled to the proximal actuator mechanism; (b) a first pinch member; (c) a second pinch member; (d) a first tension member in contact with the first pinch member; and (e) a second tension member in contact with the second pinch member. The moveable assembly includes a central block portion sized and configured to engage the first pinch member and the second pinch member and is positioned at least partially between the first pinch member and the second pinch member.

In another embodiment, the present disclosure is directed to a medical device having a deflectable distal region. The medical device comprises: (i) a handle; and (ii) a moveable assembly disposed in the handle and configured to slide along a longitudinal axis within the handle. The moveable assembly comprises: (a) a rotary member; (b) a central hub; and (c) at least four primary shafts coupled to the moveable assembly via a slide mechanism and extending into an interior of the moveable assembly wherein at least one primary shaft is positioned distal of the rotary member and is configured for contacting a distal end of the rotary member and at least one primary shaft is positioned proximal of the rotary member and configured for contacting the proximal end of the rotary member. The medical device further comprises: (iii) at least two secondary shafts positioned within the rotary member; and (iv) a pull wire coupled to the handle at a proximal end thereof and extending from the proximal end of the rotary member to the distal end of the rotary member.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 5 illustrates a catheter handle including an actuator restraining assembly disposed therein in a neutral state in accordance with multiple embodiments of the present disclosure;

FIG. 6 illustrates a catheter handle including an actuator restraining assembly disposed therein under a force along arrow Y in accordance with multiple embodiments of the present disclosure;

Corresponding reference characters indicate corresponding parts throughout the several views of the drawings. It is understood that that Figures are not necessarily to scale.

DETAILED DESCRIPTION OF THE DISCLOSURE

Figure 1:
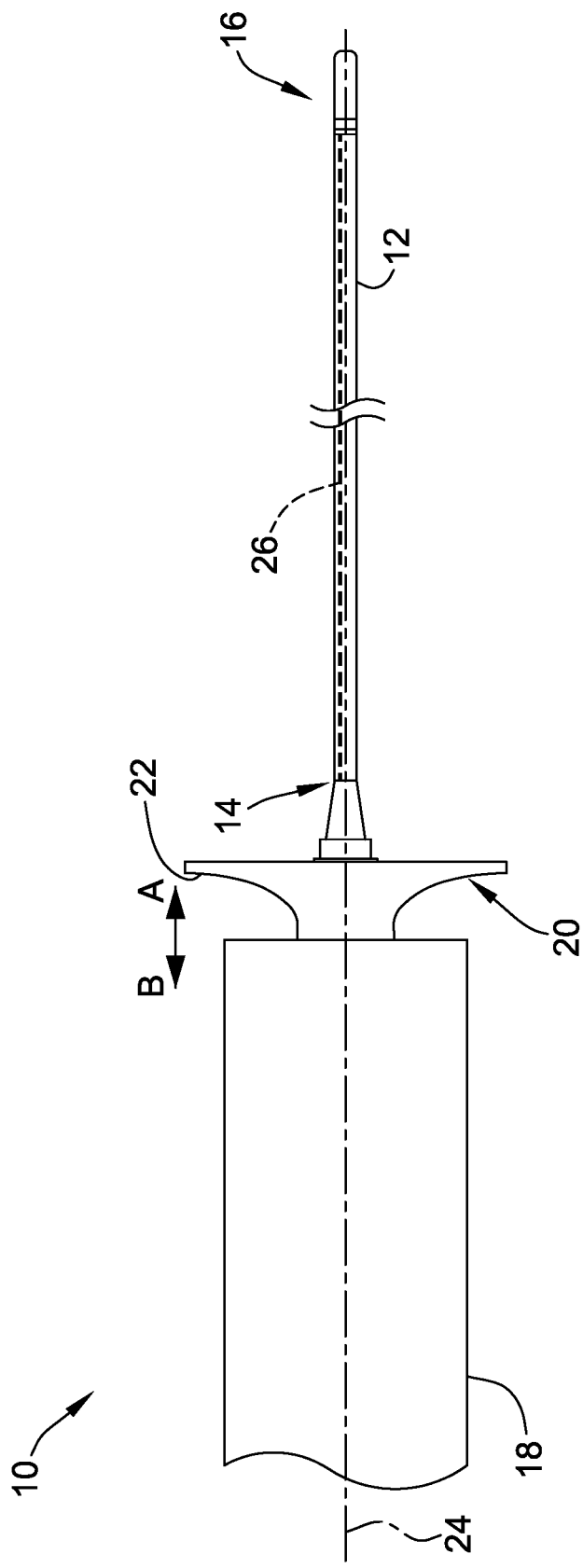
FIG. 1 is a perspective view of one embodiment of a catheter system including a handle, a catheter shaft, and an actuating mechanism.

The present disclosure provides medical devices including catheter systems suitable for use in the human vasculature for known medical procedures. Catheter systems of the multiple embodiments of the present disclosure exhibit a "self-locking" feature upon the catheter system being positioned in a deflected configuration; that is, the present disclosure provides embodiments wherein an actuator mechanism of a catheter system is restrained or locked in the position in which a distal region of the catheter system, such as the distal region of a catheter shaft, is in a deflected configuration, without the need for a user to perform an additional "locking" step to maintain the actuator mechanism in the desired position. Because the "automatic" or "self-locking" feature does not permanently fix the actuator mechanism in a particular position, the "self-locking" features disclosed herein are also reversible upon the application of a sufficient external force on the actuator mechanism in either the proximal direction (to reduce the amount of deflection of the catheter shaft) or the distal direction (to increase the amount of deflection of the catheter shaft). Such disclosed embodiments may lead to more consistent and improved patient outcomes, as well as a reduced amount of fatigue for the user. For purposes of this description, the present disclosure will be primarily described in connection with numerous embodiments of a uni-directional plunger-type catheter including an actuator restraining assembly as described herein. It is contemplated, however, that the described features and methods of the present disclosure as described herein may be incorporated into any number of uni-directional or bi-directional catheters, such as slide-based or rotational-based catheters, or other medical devices as would be appreciated by one of ordinary skill in the art based on the disclosure herein.

More specifically, some embodiments of the present disclosure provide a catheter system including an actuator restraining assembly comprising a moveable assembly disposed in a catheter handle for causing deflection of a distal region of a deflectable catheter shaft upon longitudinal movement within the handle. The moveable assembly may have two or more pinch members and tension members or a central hub and various primary and secondary shafts as described herein and may include two or more pinch points that are capable of providing a desired "locking mechanism" as described herein upon activation by pinching and holding a pull wire in a desired position. Other embodiments described herein include methods of using the catheter system including the actuator restraining assembly.

The actuator restraining assemblies as described herein provide a mechanistic way by which an actuator mechanism may be restrained, or "locked," in a particular position during use of a deflectable catheter system without the need for performing an additional locking step. That is, catheter systems including a deflectable catheter shaft known in the art oftentimes utilize an eccentric pull wire configured to interact with an actuator mechanism via a catheter shaft in order to initiate the defection of the distal region of the catheter shaft. As discussed in greater detail below, during use of catheter systems such as these, a user may advance an actuator mechanism (also referred to as an actuator lever) distally, thus causing a proximal end of the pull wire, which may be mounted or fastened to a gripper, to move along with the catheter shaft until such movement is stopped or prohibited by an obstacle (or shoulder) positioned within the handle housing. Continued distal movement of the catheter shaft, driven by the actuator mechanism, creates a high tension on the pull wire. Due to the eccentric fixation of the pull wire to the distal end of the catheter shaft, the tension on the pull wire generates the bending moment imposed on the distal region of the catheter shaft, leading to deflection of the distal region of the catheter shaft. At the same time, the tension on the pull wire leading to the deflection of the distal region results in the actuator mechanism tending to retract to a neutral (i.e., non-tensioned) state once a distal force is no longer imposed on the actuator mechanism. The various embodiments of the actuator restraining assemblies described herein provide a frictional or mechanical resistance to limit undesired and/or unintentional retraction of the actuator mechanism (thus leading to the distal region of the catheter shaft reverting to a "neutral" or "un-deflected" configuration) without the need for a user to perform an additional "locking" step. Further, because the various embodiments of the restraining assembly disclosed herein do not permanently "fix" the actuator mechanism in the position corresponding to the deflected configuration of the catheter shaft, a user is able to proximally adjust the actuator mechanism during or after a procedure to provide the distal region of the catheter shaft with less or no deflection as compared to the original deflected configuration upon the application of an additional force; that is, the restraining of the actuator mechanism in the catheter deflected position is reversible.

Figure 2:
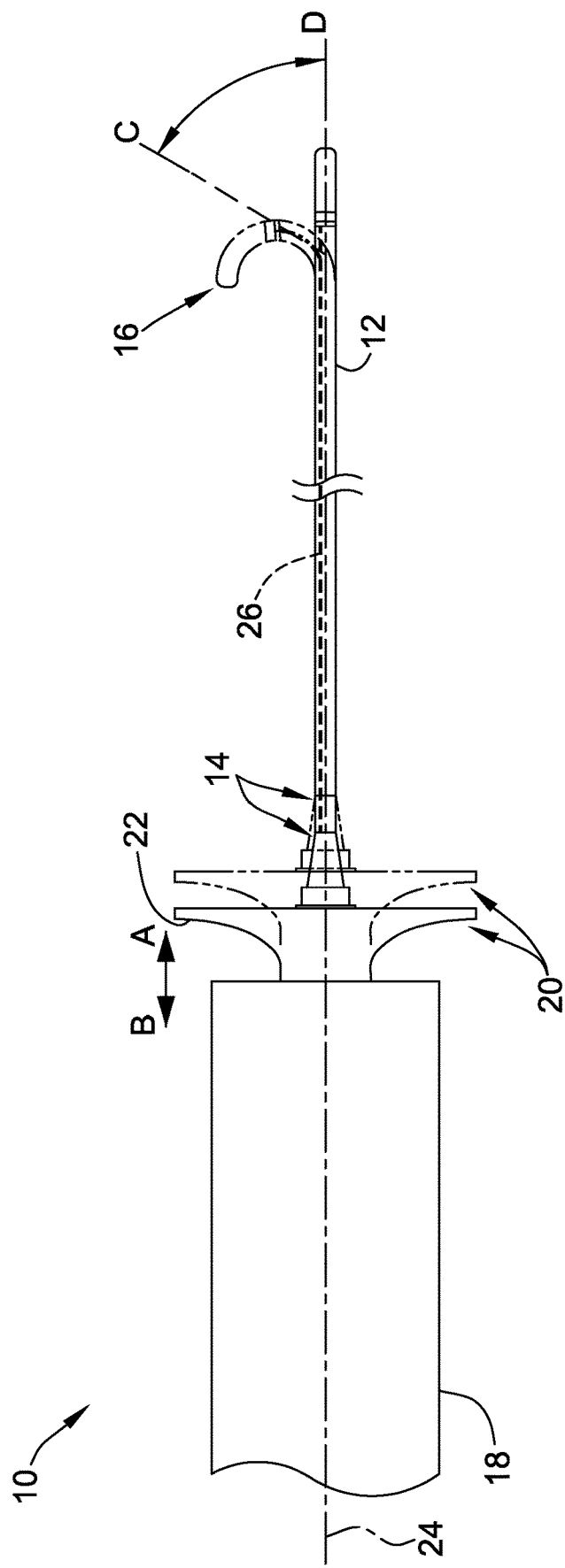
FIG. 2 illustrates the use of a pull wire to deflect the distal end of the catheter shaft of FIG. 1.

Referring now to the drawings, and specifically to FIG. 1, there is shown a plunger-type catheter 10 in an undeflected, or neutral position. Catheter 10 generally includes catheter shaft 12, having a proximal region 14 and a deflectable distal region 16, a handle 18, pull wire 26, and an actuator housing (not shown). Handle 18 includes an actuator mechanism 20. As illustrated in FIGS. 1 and 2, actuator mechanism 20 includes an drive lever 22 (also commonly referred to as an "actuator lever" or "plunger") that is moveable relative to handle 18 along a central, longitudinal axis 24 of handle 18 in a first direction along arrow A (e.g., distally) that effects deflection of distal region 16 of catheter shaft 12 from the neutral position, as well as in a second, opposite direction along arrow B (e.g., proximally) that effects return or retraction of distal region 16 toward the neutral position. For example, catheter 10 can be of the type disclosed in United States Patent Application Publication No. 20150174369, filed Sep. 30, 2013 and published Jun. 25, 2015, which is hereby incorporated by reference as though fully set forth herein.

Referring now to FIG. 2 the use of pull wire 26 for deflecting distal region 16 of catheter shaft 12 is illustrated. Pull wire 26 extends through a lumen (not shown) of catheter shaft 12. Pull wire 26 is coupled to a pull ring (not shown) embedded in distal region 16 of catheter shaft 12 and to a gripper (not shown), such that movement of drive lever 22 in the first direction along arrow A effects deflection of distal region 16 of catheter shaft 12 from the neutral position along a first deflection direction (e.g., arrow C), and such that movement of drive lever 22 in the second direction along arrow B effects the return or retraction of distal region 16 of catheter shaft 12 towards the neutral position (e.g., along arrow D). Insofar as a person of ordinary skill in the art will appreciate the use of pull wires in a catheter, a detailed explanation of this aspect of the disclosure is not provided herein.

Although the catheter systems disclosed herein are described primarily with respect to uni-directional catheters, it should be recognized as noted above that the disclosed principles are equally applicable in other contexts, including but not limited to, bi-directional catheters and other medical devices. That is, for example, with various structural arrangements of the restraining assembly discussed below, movement of drive lever 22 in the first direction along arrow A (See FIG. 2) could affect deflection of deflectable distal region 16 from the neutral position in a first defection direction (e.g., arrow C in FIG. 2), while movement of drive lever 22 in the second direction could affect deflection of deflectable distal region 16 from the neutral position in a second deflection direction, with both the first and second deflection directions lying in the same plane.

Plunger-type catheter 10 as illustrated in FIGS. 1 and 2 may further include an actuator restraining assembly configured to further restrain catheter shaft 12 in a position corresponding to a deflected configuration of deflectable distal region 16 without the need for an additional "locking" step being performed by a user (i.e., the restraining assembly is "self-locking"). That is, the restraining assembly is configured such that upon a user distally advancing drive lever 22 into a first position along arrow A (See FIG. 2) and thus deflecting deflectable distal region 16, the restraining assembly remains in the first position, thus holding deflectable distal region 16 in the desired deflected configuration upon a user no longer applying any force on drive lever 22. The restraining assembly is also configured to be releasable upon the application of a distal force (i.e., direction A in FIG. 2) or a proximal force (i.e., direction B in FIG. 2) on drive lever 22. As is described in more detail below, the restraining assembly exerts a frictional or mechanical force arising between components thereof and an inner wall of a handle. That is, the restraining assembly may provide a normal force and a frictional resistance against its impending movement with respect to a handle in a proximal direction (i.e., along arrow B) until a sufficient driving force is applied to drive lever 22 to overcome the frictional resistance exerted by the restraining assembly.

Figure 3:
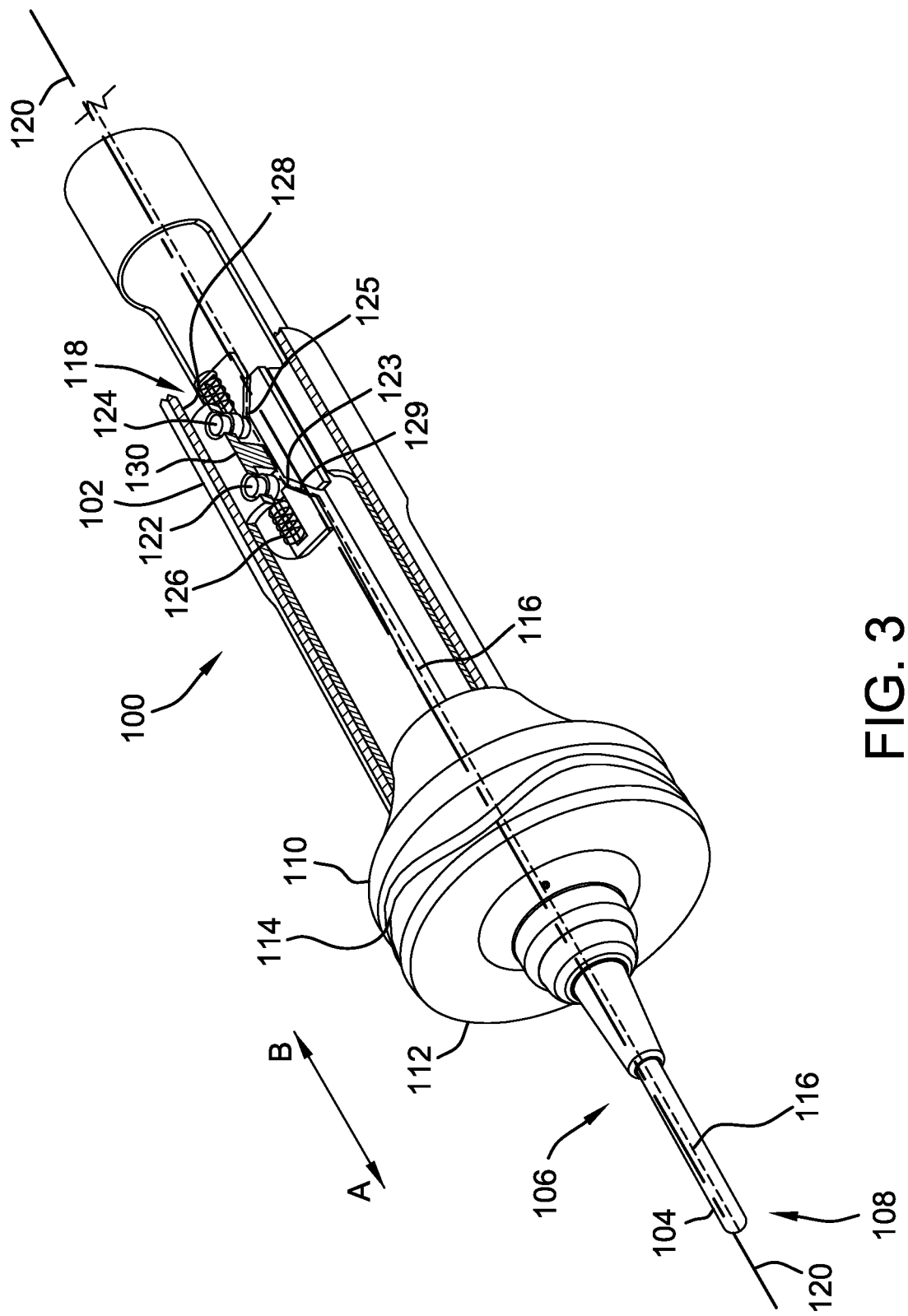
FIG. 3 is a partial cut-away view of a catheter with a deflectable distal region in a neutral position and including an exemplary actuator restraining assembly in accordance with multiple embodiments of the present disclosure.

Referring now to FIG. 3 and in accordance with the various embodiments of the present disclosure, there is illustrated a partial cut-away view of a plunger-type catheter 100. Plunger-type catheter 100 includes handle 102, catheter shaft 104 having proximal region 106 and deflectable distal region 108 (shown in the neutral, or "un-deflected" position), proximal actuator mechanism 110, distal actuator mechanism 112, and actuator spring 114, illustrated herein as a single wave spring. Plunger-type catheter 100 further includes pull wire 116 coupled to deflectable distal region 108 to effect deflection of distal region 108. Plunger-type catheter 100 further includes moveable assembly 118 disposed in handle 102 and fixedly coupled to proximal actuator mechanism 110 and further configured to slide along longitudinal axis 120 of handle 102 upon the application of a force along longitudinal axis 120. Moveable assembly 118 further includes first pinch member 122, second pinch member 124, first tension member 126 in contact with first pinch member 122, second tension member 128 in contact with second pinch member 124, and guide channel 129 for guiding pull wire 116 through moveable assembly 118 and for allowing pull wire 116 to be in contact with first pinch member 122 at first pinch point 123 and second pinch member 124 at second pinch point 125. Additionally, moveable assembly 118 includes central block portion 130 configured to be positioned at least partially between first pinch member 122 and second pinch member 124 such that central block portion 130 is in contact with first pinch member 122 and second pinch member 124. Because first pinch member 122 is in contact with first tension member 126 and central block portion 130 and second pinch member 124 is in contact with second tension member 128 and central block portion 130, first pinch member 122 and second pinch member 124 pinch pull wire 116 in guide channel 129 and hold pull wire 116 in a desired position until a force is applied along longitudinal axis 120 as described herein.

In many embodiments, first pinch member 122 and second pinch member 124 may be rollers that are comprised of a high friction material, such as a silicone material, although other configurations and materials for first pinch member 122 and second pinch member 124 are within the scope of the present disclosure. In many embodiments, first tension member 126 and second tension member 128 may be compressible springs, although other types of compression members including shock absorbers and the like are within the scope of the present disclosure.

In many embodiments of the present disclosure, the pull wires described herein for causing deflection of the distal region of catheter shaft may be conventional pull wires formed from conventional metals and the like. In some embodiments, the portion of the pull wire that is in contact with the actuator restraining assembly may be comprised partially or completely of a Kevlar® or similar para-aramid synthetic fiber material to improve resistance to wear and provide a smooth action during deflection and un-deflection. In some embodiments, a Kevlar® or other para-aramid synthetic fiber material may be connected, attached, or coupled to a conventional pull wire (bonded, glued, welded, crimped, etc.) such that overall resistance to failure is improved by the combination.

In use, movement of proximal actuator mechanism 110 and distal actuator mechanism 112 in a direction along arrow A as illustrated in FIG. 3 (or distally with respect to handle 102) causes movement of moveable assembly 118 in the same direction, for example to deflect deflectable distal region 108 of catheter shaft 104, while movement of distal actuator mechanism 112 and proximal actuator mechanism 110 in a direction along arrow B as illustrated in FIG. 3 (or proximally with respect to handle 102) causes movement of moveable assembly 118 in the same direction, for example to release deflection of distal region 108 of catheter shaft 104 to a neutral or un-deflected position. As moveable assembly 118 is moved or forced in a direction along arrow A, central block portion 130 contacts first pinch member 122 and compresses it against first tension member 126, thus moving first pinch member 122 and releasing the pinching of pull wire 116 at first pinch point 123 and allowing pull wire 116 to be able to move in the same direction as the applied force to allow deflection of deflectable distal region 108 of catheter shaft 104. When the force along arrow A is eliminated and central block portion 130 is no longer compressing first pinch member 122 against first tension member 126, first pinch member 122 moves back to its neutral, un-compressed position again pinching pull wire 116 and not allowing pull wire 116 to move further. This pinching results in a "locking" feature that keeps deflectable distal region 108 of catheter shaft 104 deflected.

Figure 4:
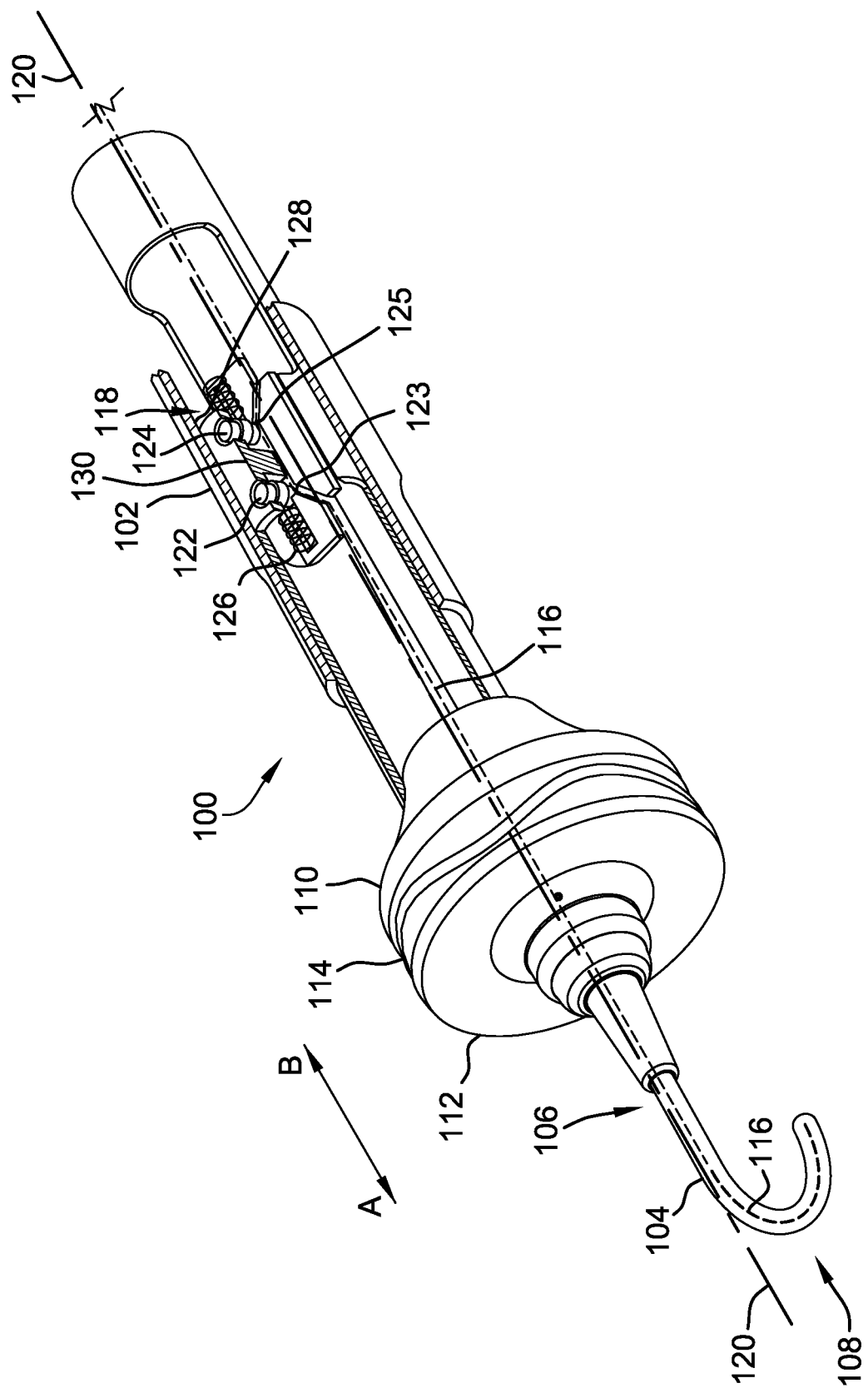
FIG. 4 is a partial cut-away view of the catheter of FIG. 3 with a deflectable distal region in a deflected position and including an exemplary actuator restraining assembly in accordance with multiple embodiments of the present disclosure.

Referring now to FIG. 4, there is shown a partial cut-away view of plunger-type catheter 100 including catheter shaft 104 having proximal region 106 and deflectable distal region 108 in a deflected position. By applying force along arrow A as described above, moveable assembly 118 has moved along arrow A out of handle 102 allowing for the deflection of deflectable distal region 108. As noted, once the force along arrow A is discontinued, first pinch member 122 and second pinch member 124, through the compression of first tension member 126 and second tension member 128 against central block portion 130 again pinch pull wire 116 at first pinch point 123 and second pinch point 125 thus securing it and maintaining the desired deflection of deflectable distal region 108.

In further use, and referring again to FIGS. 3 and 4, deflectable distal region 108 of catheter shaft 104 may be un-deflected or returned to a neutral state by applying a force to proximal actuator mechanism 110 and distal actuator mechanism 112 in a direction along arrow B such that assembly 118 moves along arrow B. Such a force causes central block portion 130 to contact second pinch member 124 and compresses it against second tension member 128, thus moving second pinch member 124 and releasing the pinching of pull wire 116 at second pinch point 125 and allowing pull wire 116 to be able to move in the same direction as the applied force (along arrow B) to allow deflection of deflectable distal region 108 of catheter shaft 104 to be eliminated such that deflectable distal region 108 can be returned to a neutral position. When the force along arrow B is eliminated and central block portion 130 is no longer compressing second pinch member 124 against second tension member 128, second pinch member 124 moves back to its neutral, un-compressed position again pinching pull wire 116 and not allowing pull wire 116 to move further. The relative movement of assembly 118 (that is, how easy or difficult assembly 118 moves along arrow A and arrow B) may be controlled and adjusted by any suitable means to provide the desired resistance to movement of assembly 118. For example, friction between assembly 118 and the inner wall of the handle may be provided to control the resistance and pressure required to move assembly 118. Such friction may be provided by the meshing of one or more gears and/or by providing a textured inner wall of the handle to increase the coefficient of friction between assembly 118 and the inner wall of the handle. Friction to control the movement of assembly 118 may also be provided in some embodiments by knurling first pinch member 122 and/or second pinch member 124.

In another embodiment of the present disclosure, a locking feature for securing deflection of a distal region of a catheter shaft may be provided using a rotational-based locking feature as compared to the longitudinal-based locking feature described above. The rotational-based locking feature may be particularly useful in catheter systems that utilize a sliding-type mechanism (as opposed to a plunger-type mechanism) to effectuate deflection. In this configuration, the slide mechanism may be slidably disposed on an outer surface of the catheter handle. Referring now to FIG. 5 and in accordance with the various embodiments of the present disclosure, there is illustrated a top view of a moveable assembly 200 disposed in handle 202 and configured to slide along longitudinal axis 204 within handle 202. Moveable assembly 200 has proximal end 206 and a distal end 208. Moveable assembly 200 includes rotary member 210 having distal end 211 and proximal end 213, central hub 212, and primary shafts 214, 216, 218, and 220. Rotary member 210 and primary shafts 214, 216, 218, and 220 are coupled to moveable assembly 200 via a slide mechanism (not shown in FIG. 5 but generally present on an exterior surface of handle 202) and extend into an interior of moveable assembly 200. Primary shaft 214 is positioned distal of rotary member 210 and is configured for contacting distal end 211 of rotary member 210. Primary shaft 220 is positioned proximal of rotary member 210 and is configured for contacting proximal end 213 of rotary member 210. Primary shafts 214 and 220 are positioned so as to ensure that pull wire 226 comes into moveable assembly 200 substantially centered to minimize or eliminate the potential for eccentric loading and resulting increased friction.

Referring again to FIG. 5, moveable assembly 200 further includes secondary shaft 222 and secondary shaft 224, each positioned within rotary member 210. Secondary shaft 222 is secured to central hub 212 and secondary shaft 224 is secured to central hub 212 to assist in rotation of rotary member 210 upon the application of a force as further described herein. A pull wire 226 extends from proximal end 213 to distal end 211 of rotary member 210 and is coupled to handle 202 at a proximal end thereof at a location not shown in FIG. 5 and to a deflectable distal region of a catheter shaft also not shown in FIG. 5. In many embodiments, pull wire 226 is positioned around at least part of an outer circumference of each of central hub 212, primary shafts 214, 216, 218, and 220 and secondary shafts 222 and 224. As noted above, suitable pull wires may be conventional pull wires or hybrid pull wires including a second wire, filament, or strand. Secondary shaft 222 and primary shaft 216 form first pinch point 228 and secondary shaft 224 and primary shaft 218 form second pinch point 230. Rotary member 210 can rotate and move within openings 232 and 234 upon the application of a force as described herein. Although not illustrated in the Figures, one or more components (in addition to primary shafts 214 and 220) of the moveable assembly in contact with pull wire 226 may optionally include a guide channel or positioning groove therein or thereon to facilitate control of the location of pull wire 226 on the component such that pull wire 226 remains in a constant, desired vertical position on the component during usage.

In use, movement of the slide mechanism (not shown in FIG. 5) located on handle 202 along arrow Y as shown in FIG. 6 (or distally with respect to handle 202) causes movement of rotary member 210 as illustrated in FIG. 6. As the force is applied along arrow Y by the slide mechanism, rotary member 210 rotates counterclockwise. This counterclockwise rotation causes separation between primary shaft 216 and secondary shaft 222 and between primary shaft 218 and secondary shaft 224 thus relieving first pinch point 228 and second pinch point 230 such that pull wire may move freely during the application of force along arrow Y and result in the desired deflection. Once the force along arrow Y is removed, rotary member 210 returns to its neutral position again locking pull wire 226 in place at first pinch point 228 and second pinch point 230 to provide the desired locking feature. In many embodiments described herein, pull wire 226 is continually under tension; this continuous tension may be provided by any suitable means including, for example, through the use of a small tension member (such as a spring) at the connection point of pull wire 226 and the handle. This tension provides the constant force needed to return rotary member 210 back to its neutral position.

Figure 7:
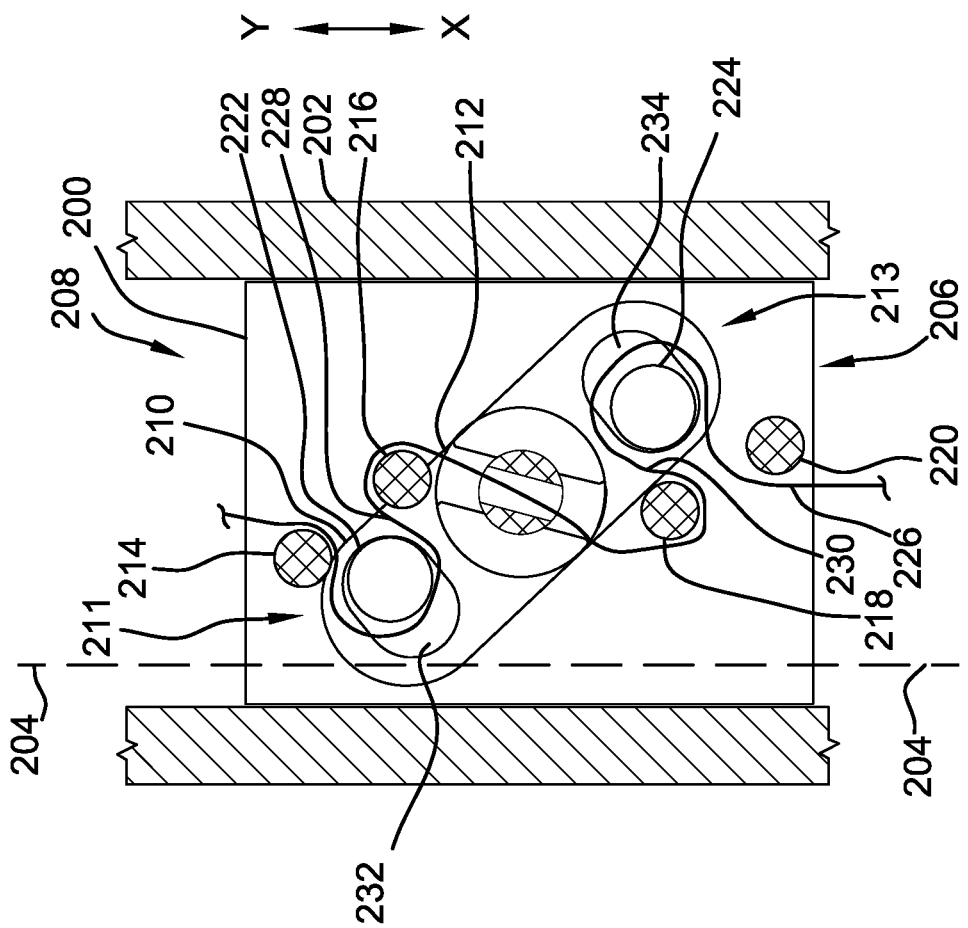
FIG. 7 illustrates a catheter handle including an actuator restraining assembly disposed therein under a force along arrow X in accordance with multiple embodiments of the present disclosure.

In further use, and referring now to FIGS. 5, 6, and 7 the distal region of a catheter shaft may be un-deflected or returned to a neutral state by applying a force to the slide mechanism along arrow X. Such a force again causes rotary member 210 to rotate counterclockwise and result in separation between primary shaft 216 and secondary shaft 222 and between primary shaft 218 and secondary shaft 224 thus relieving first pinch point 228 and second pinch point 230 such that pull wire may move freely during the application of force along arrow X and result in the desired un-deflection. Once the force along arrow X is removed, rotary member 210 returns to its neutral position again locking pull wire 226 in place at first pinch point 228 and second pinch point 230 to restrict movement of pull wire 226.

Other embodiments of the present disclosure include methods of using the medical devices described herein, and particularly to using a slide-type catheter including an actuator restraining assembly as described herein. In one specific embodiment, a method of deflecting the distal region of a medical device, such as the distal region of a catheter shaft, is disclosed. In this embodiment, the method comprises first providing a medical device including a catheter shaft having a proximal region and a deflectable distal region and an active drive assembly comprising an actuator mechanism that is configured to engage the proximal region of the catheter shaft and is at least partially movable with respect to a handle along a longitudinal axis thereof. The medical device further includes an actuator restraining assembly as described hereinabove. The actuator restraining assembly includes a moveable assembly disposed in the catheter handle that is fixedly coupled to the proximal actuator mechanism, a first pinch member, a second pinch member, a first tension member in contact with the first pinch member, and a second tension member in contact with the second pinch member. The moveable assembly further includes a central block portion sized and configured to engage the first pinch member and the second pinch member. The central block portion is positioned at least partially between the first pinch member and the second pinch member. With this method, including the actuator restraining assembly, an operator can deflect the distal portion of a catheter shaft and lock it in place during a procedure such that the operator is subject to less fatigue during the procedure.

Other embodiments of the present disclosure include methods of using the medical devices described herein, and particularly to using a plunger-type catheter including an actuator restraining assembly as described herein. In one specific embodiment, a method of deflecting the distal region of a medical device, such as the distal region of a catheter shaft, is disclosed. In this embodiment, the method comprises first providing a medical device including a catheter shaft having a proximal region and a deflectable distal region and an active drive assembly comprising a split actuator mechanism that is configured to engage the proximal region of the catheter shaft and is at least partially movable with respect to a handle along a longitudinal axis thereof. The medical device further includes an actuator restraining assembly as described hereinabove. The actuator restraining assembly includes a moveable assembly disposed in the handle and configured to slide along a longitudinal axis within the handle. The moveable assembly comprises a rotary member, a central hub and at least four primary shafts coupled to the moveable assembly via a slide mechanism and extending into an interior of the moveable assembly. At least one primary shaft is positioned distal of the rotary member and is configured for contacting a distal end of the rotary member and at least one primary shaft is positioned proximal of the rotary member and configured for contacting the proximal end of the rotary member. At least two secondary shafts positioned within the rotary member. With this method, including the actuator restraining assembly, an operator can deflect the distal portion of a catheter shaft and lock it in place during a procedure such that the operator is subject to less fatigue during the procedure.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A medical device having a deflectable distal region, the medical device comprising:
   a handle;
   a moveable assembly disposed in the handle and configured to slide along a longitudinal axis within the handle, the moveable assembly comprising;
   a rotary member;
   a central hub and at least four primary shafts coupled to the moveable assembly via a slide mechanism and extending into an interior of the moveable assembly, wherein at least one primary shaft is positioned distal of the rotary member and is configured for contacting a distal end of the rotary member and at least one primary shaft is positioned proximal of the rotary member and configured for contacting a proximal end of the rotary member;
   at least two secondary shafts positioned within the rotary member; and
   a pull wire coupled to the handle at a proximal end thereof and extending from the proximal end of the rotary member to the distal end of the rotary member.

2. The medical device of claim 1, wherein the slide mechanism is configured to move the moveable assembly in a longitudinal direction relative to the handle to facilitate deflection of a distal portion of the medical device.

3. The medical device of claim 1, wherein the pull wire is positioned around at least part of an outer circumference of each of the central hub, the at least four primary shafts, and the at least two secondary shafts.

4. The medical device of claim 1, wherein the rotary member is coupled to the slide mechanism via the central hub.

5. The medical device of claim 1, wherein the slide mechanism and at least four primary shafts are configured with respect to the rotary member such that longitudinal movement of the slide mechanism causes the rotary member to rotate with respect to the handle.

6. The medical device of claim 1, wherein the at least four primary shafts are positioned with respect to the at least two secondary shafts such that longitudinal movement of the slide mechanism and the at least four primary shafts creates a gap between at least one primary shaft and at least one secondary shaft for passage of the pull wire therethrough.

7. The medical device of claim 1, wherein the pull wire is configured with respect to the at least four primary shafts and the at least two secondary shafts such that rotation of the rotary member causes a tension to be applied to the pull wire.

8. A medical device comprising:
   a handle;
   a moveable assembly disposed in the handle and configured to slide along a longitudinal axis within the handle, the moveable assembly comprising;
   a rotary member;
   a central hub and at least two primary shafts coupled to the moveable assembly via a slide mechanism and extending into an interior of the moveable assembly, wherein at least one primary shaft is positioned distal of the rotary member and is configured for contacting a distal end of the rotary member and at least one primary shaft is positioned proximal of the rotary member and is configured for contacting a proximal end of the rotary member;
   at least two secondary shafts positioned within the rotary member; and
   a pull wire extending from the proximal end of the rotary member to the distal end of the rotary member.

9. The medical device of claim 8, wherein the slide mechanism is configured to move the moveable assembly in a longitudinal direction relative to the handle to facilitate deflection of a distal portion of the medical device.

10. The medical device of claim 8, wherein the pull wire is positioned around at least part of an outer circumference of each of the central hub, the at least two primary shafts, and the at least two secondary shafts.

11. The medical device of claim 8, wherein the rotary member is coupled to the slide mechanism via the central hub.

12. The medical device of claim 8, wherein the slide mechanism and at least two primary shafts are configured with respect to the rotary member such that longitudinal movement of the slide mechanism causes the rotary member to rotate with respect to the handle.

13. The medical device of claim 8, wherein the at least two primary shafts are positioned with respect to the at least two secondary shafts such that longitudinal movement of the slide mechanism and the at least two primary shafts creates a gap between at least one primary shaft and at least one secondary shaft for passage of the pull wire therethrough.

14. The medical device of claim 8, wherein the pull wire is configured with respect to the at least two primary shafts and the at least two secondary shafts such that rotation of the rotary member causes a tension to be applied to the pull wire.

15. A method of assembling a medical device, the method comprising:
   providing a handle; and
   coupling a moveable assembly to the handle, the moveable assembly configured to slide within the handle along a longitudinal axis, the moveable assembly including;
   a rotary member;
   a central hub and at least four primary shafts coupled to the moveable assembly via a slide mechanism and extending into an interior of the moveable assembly, wherein at least one primary shaft is positioned distal of the rotary member and is configured for contacting a distal end of the rotary member and at least one primary shaft is positioned proximal of the rotary member and configured for contacting a proximal end of the rotary member;
   at least two secondary shafts positioned within the rotary member; and
   a pull wire coupled to the handle at a proximal end thereof and extending from the proximal end of the rotary member to the distal end of the rotary member.

16. The method of claim 15, wherein the slide mechanism is configured to move the moveable assembly in a longitudinal direction relative to the handle to facilitate deflection of a distal portion of the medical device.

17. The method of claim 15, wherein the pull wire is positioned around at least part of an outer circumference of each of the central hub, the at least four primary shafts, and the at least two secondary shafts.

18. The method of claim 15, wherein the rotary member is coupled to the slide mechanism via the central hub.

19. The method of claim 15, wherein the slide mechanism and at least four primary shafts are configured with respect to the rotary member such that longitudinal movement of the slide mechanism causes the rotary member to rotate with respect to the handle.

20. The medical device of claim 15, wherein the at least four primary shafts are positioned with respect to the at least two secondary shafts such that longitudinal movement of the slide mechanism and the at least four primary shafts creates a gap between at least one primary shaft and at least one secondary shaft for passage of the pull wire therethrough.

* * * * *